United States Patent [19]

Bodor

[11] Patent Number: 4,594,356
[45] Date of Patent: Jun. 10, 1986

[54] METHOD FOR INDUCING MYDRIASIS IN ANIMALS

[75] Inventor: Nicholas Bodor, Gainesville, Fla.

[73] Assignee: Key Pharmaceuticals, Inc., Miami, Fla.

[21] Appl. No.: 689,765

[22] Filed: Jan. 8, 1985

[51] Int. Cl.⁴ .................... A61K 31/22; A61K 31/24; A61K 31/225; A61K 31/235

[52] U.S. Cl. ................................... 514/534; 514/532; 514/536; 514/548; 514/551; 514/912

[58] Field of Search ............... 514/532, 534, 536, 548, 514/551, 912

[56] References Cited

U.S. PATENT DOCUMENTS 3,908,017 9/1975 Hussain et al. ............... 424/311
3,922,348 11/1975 Seidehamel et al. ........... 424/330
4,094,983 6/1978 Boder ........................... 424/266

OTHER PUBLICATIONS

Chem. Abst. 101, 183,396(e) (1984)–Bodor et al.

Primary Examiner—Douglas W. Robinson
Attorney, Agent, or Firm—Ronald G. Ort

[57] ABSTRACT

A method of inducing short-term pupil diameter enlargement and reducing intraocular pressure in animals without significant systemic effects is disclosed. There is provided a site-specific chemical delivery method for topically applying to the eye of an animal, an effective ophthalmologically acceptable amount of an adrenalone diester of the general formula:

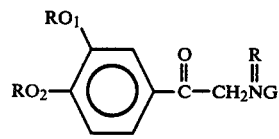

Formula I wherein R prepresents a member selected from the group consisting of hydrogen or a $C_1$–$C_3$ straight alkyl group; and wherein $R_1$ and $R_2$ independently represent an acyl group or derivative thereof; or an opthalmologically acceptable acid addition salt thereof. The method allows the pupil diameter to be enlarged for a short period after which the pupil returns to normal and thus restores normal eye sight.

14 Claims, No Drawings

METHOD FOR INDUCING MYDRIASIS IN ANIMALS

FIELD OF THE INVENTION

The present invention relates to a new site-specific chemical delivery system for inducing mydriasis (pupil diameter enlargement) and for reducing intraocular pressure in animals for a limited duration through the use of a select group of adrenalone diesters and the non-toxic, but opthalmologically effective pharmaceutically acceptable acid addition salts thereof, and pharmaceutical compositions containing them.

BACKGROUND OF THE INVENTION

Mydriatic agents are an important class of compounds that are used to dilate the pupil. Mydriasis is required during opthalmic examinations, in order to provide for a more complete examination of the fundus, the vitreous and the periphery of the lens, and in various surgical procedures such as those reported by Freeman and Gettelfinges, *American Intra-Ocular Implant Society Journal*, 7,172–173 (1981) (e.g. vitrectomy, lens extraction, and intraocular lens implantation).

A clinical study reported by R. Weekers, et al., *American Journal of Opthalmology*, 40,666–672 (1955) concluded that reduced ocular tension results from sympathomimetic stimulation. Included in the study were such diverse sympathomimetic (adrenergic) amines as adrenalone (the corresponding ketone derivative of adrenalin) and the dextrorotatory (d) and levorotatory (l) optical isomers of adrenalin (epinephrine). The study established that 1-adrenaline (a strong sympathomimetic agent) lowered ocular tension, whereas the corresponding derivative, adrenalone and d-adrenalin (agents having only minimal sympathomimetic activity) do not. Even a 2% adrenalone solution did not cause any reduction in the intraocular pressure of patients suffering from glaucoma, and resulted in only a minimal level of mydriatic activity.

The primary objective of the prior art was to reduce the intraocular pressure in the treatment of glaucoma, an eye disease characterized by a progressive increase in intraocular pressure that occurs over a prolonged period of time. The drugs used were intended to have a long acting effect in order to keep the pressure down over a long period of time without need for readministration of the drug. If left untreated, the optic nerve will deteriorate to such an extend that blindness occurs. To reduce the intraocular pressure sufficiently to prevent damage to the optic nerve, the adrenergic amine, epinephrine, and miotics, which include certain parasympathomimetics such as pilocarpine and cholinesterase inhibitors such as physostigmine, have been applied topically to the eye. However, undesirable side effects were observed. Absorption of the topically applied drug occasionally causes systemic effects as well as localized allergic reactions. The alpha-adrenergic stimulatory action of epinephrine frequently causes mydriasis and sometimes retinal maculopathy, during prolonged usage.

Isoproterenol, another adrenergic amine, had satisfactorily reduced intraocular pressure while also causing mydriasis. However, such serious side-effects as taachycardia, weakness, and palpatations were observed so that the continued practical use of this drug in the treatment of glaucoma was prohibited. Ross and Drance, *Arch. Ophthal.*, 83, 39–43 (1920).

U.S. Pat. Nos. 3,959,485, 3,839,584 and 3,868,461 and 3,959,485 all disclose the use of chemically modified sympathomimetic amines in the treatment of glaucoma and other ailments receptive to sympthomimetic amine activity. Specifically, the dipivaloxy derivatives of epinephrine and isoproterenol are disclosed.

U.S. Pat. No. 3,922,348 discloses successful treatment of glaucoma with a compound designated as 3,4-dihydroxy-2-(isopropylamino) acetophenone, the corresponding ketone derivative of isoproterenol. A review of the reference reveals that a high concentration (3%) is needed to achieve the desired result. Additionally, mydriatic activity is termed a toxic, harmful or deleterious side-effect.

Ocular tissues have the ability to metabolize a wide variety of drugs and foreign chemicals (powerful metabolic system for the biotransformation of exogenous substances). Since the eye is a relatively isolated organ that tends to retain or concentrate compounds within itself as described by Shichi and Nebert in *Extrahepatic Metabolism of Drugs and Other Foreign Compounds* (Gram, T., ed.) 333–363, S.P. Medical and Scientific Books, New York (1980), compounds applied or carried by the bloodstream to the eye must be detoxified. Considering that the uveal (iris-ciliary body) tissues have the largest blood flow of any tissue in the body, it seems reasonable that these tissues would have the best developed drug metabolizing system found in the eye. This has been substantiated by a number of research groups. Das, and Shichi, *Expt. Eye Res.*, 33, 525–533 (1981). Drug metabolism by reduction of ketones and aldehydes has been established to be a preferential enzymatic pathway in mammals. Felsted and Bachur, *Drug Meta. Rev.*, 11, 1–60 (1980); Ahmed, Felsted and Bachur, *J. Pharmacol Exp. Ther.*, 209, 12–19 (1979). This process simultaneously eliminates lipid-soluble carbonyls and transforms them into alcohols that are significantly more polar and prepares the substrate for conjugation and elimination.

In most studies dealing with the transport and the disposition of topically applied ophthalmic agents, the anterior chamber has been considered to be the target area. Patton in *Ophthalmic Drug Delivery Systems* (Robinson ed.) Symposium Proceedings of Academy of Pharm. Sci., Chapter 2, 28–54, Washington D.C. (1980). However, since the iris-ciliary body appears to be one of the major sites of drug metabolism in the eye, it is considered to be the target tissue and its response with time can be assumed to reflect the amount of drug present.

The concept of developing methods for site-specific delivery of biologically active agents is highly desirable to improve efficacy and decrease toxicity. Although a lot of work has been done in this area, very few examples have promised simple and successful solutions. Shaw, *Annu. Rep. Med. Chem.*, 15, 302 (1980) and Bodor and Farag, *J. Med. Chem.*, 26, 313–318 (1983).

Adrenalone delivered at high concentrations will not produce mydriasis, either directly or indirectly. R. Weekers, et al, supra; Bodor and Visor, *Exp. Eye Res.*, 38, 621–626 (1984). Thus, topical administration of adrenalone results only in adrenalone delivery which is not reduced in the eye to the active adrenalin.

High ocular sympathomimetic activity of some adrenalone diesters, such as the diisovaleryl and dipivalyl derivatives were described by Bodor, Kaminsk and Roller, supra, and found to be more potent on a molar basis than the successful prodrug of epinephrine, dipivalyl epinephrine. U.S. Pat. No. 4,094,983 discloses a method for reducing intraocular pressure using the adrenalone diester dipivalyl by the present inventor of record. A review of the reference reveals that the compound did not achieve faster recovery of normal vision.

Prior studies were primarily directed to attempting to reduce intraocular pressure with a concomitant diminution mydriatic effect. While a mydriatic effect is useful for lowering intraocular pressure associated with glaucoma, it results in vision impairment which is considered an undesirable effect, whether a single or multiple drug dose is required. However, for ophthalmic examinations and various surgical procedures, as well as a short-term reduction in intraocular pressure, a need exists for a method to produce a dramatic mydriatic effect and to reduce the time it takes for recovery of normal pupil diameter and vision while remaining essentially free from the deleterious disadvantages associated with previously used compounds.

SUMMARY OF THE INVENTION

The present invention provides a method for inducing pupil diameter enlargement (mydriasis) and reducing intraocular pressure in the eye of an animal.

A primary object of the invention is to provide a method for inducing pupil diameter enlargement for a very short period of time so that normal vision can be restored relatively soon.

Another object of this invention is to provide a novel and useful type of site-specific chemical delivery system that allows for facile membrane transport and more efficient intraocular (iris-ciliary body) formulation of adrenalin, the active mydriatic inducing component, to achieve short-term extensive pupil enlargement and lower intraocular pressure thus reducing the time it takes for recovery of normal pupil diameter and vision. These and other objects are obtained by topically administering to the eye of an animal, an effective ophthalmologically amount of an adrenalone diester selected from the group consisting of the general formula:

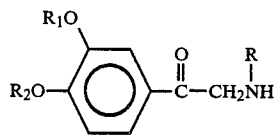

wherein R represents a member selected from the group consisting of hydrogen or a $C_1$–$C_3$ straight alkyl group; and wherein $R_1$ and $R_2$, which may be the same or different, represents an acyl group or derivative thereof; or an ophthalmologically acceptable acid addition salt thereof that can be administered in standard pharmacological formulations.

Another object of the invention is to provide a novel and useful type of site-specific chemical delivery system that is essentially free of any toxic effects resulting from non-iris-ciliary body exposure to the active specie, adrenalin.

Still another object of the invention is to provide the new type of site-specific chemical delivery system as a useful and beneficial diagnostic, surgical and therapeutic agent that induces pupil diameter enlargement and reduces intraocular pressure for use in the pharmaceutical, medical or veterinarian arts when administered to the eye of an animal.

Other objects, features and advantages of the invention will be apparent to those skilled in the art from the detailed description of the invention which follows, taken in conjunction with the accompanying claims.

DETAILED DESCRIPTION OF THE INVENTION

All of the foregoing objects, features and advantages of the present invention are readily attained by topically administering to the eye an effective ophthalmological amount on an adrenalone diester as defined by the general Formula I.

While all of the compounds within Formula I suffice for the purpose of this application, a preferred group of compounds having exceptional activity at minimal concentration exists as noted below:

(1) 0,0-di(ethylsuccinyl) adrenalone hydroperchlorate
(2) 0,0-bis(N,N-diethylsuccinamyl) adrenalone hydrochloride
(3) 0,0-dicinnamoyl-adrenalaone hydrochloride The free base derivative can be reacted with an excess of the chosen ophthalmologically acceptable HX acid (wherein "X" represents an ophthalmologically acceptable acid addition salt anion as later described) to thus obtain the corresponding ophthalmologically acceptable acid addition salt. This procedure is standard and well-known to those skilled in the art of pharmaceutical research. Additionally, adrenalone hydrochloride may be used as the starting material.

Specific examples of $R_1$ and $R_2$ acyl groups or derivatives thereof which have been found to be useful in connection with the present invention and are preferred are put forth below:

| | |
|---|---|
| $C_2H_5OCCH_2CH_2CO-$<br>$\parallel$<br>$O$ | 1. |
| $CH_3CH_2CH_2CO-$ | 2. |
| $CH_3(CH_2)_4CO-$ | 3. |
| $(C_2H_5)_2NCCH_2CH_2CO-$<br>$\parallel$<br>$O$ | 4. |
| $C_6H_5-CH-CH-CO-$ | 5. |
| $(CH_3)_2CHCH_2CO-$ | 6. |
| $(CH_3)_3CCO-$ | 7. |

Further, it should be noted that R is preferrably methyl. When R is methyl and $R_1$ and $R_2$ are simultaneously one of the group (1)–(7) above, the half-life of the resulting adrenalone diester compound was found to be as follows:

| | $R_1 = R_2$ | $t\frac{1}{2}$ Min. |
|---|---|---|
| $[t\frac{1}{2}$ (min)] = | (1) | 1.01 |
| = | (2) | 2.13 |
| = | (3) | 2.96 |
| = | (4) | 8.55 |
| = | (5) | 10.1 |
| = | (6) | 19.2 |
| = | (7) | 57.8 |

When R is methyl the half-life of the adrenalone diester compound varies as the $R_1$ and $R_2$ groups are changed as shown by the above data. Accordingly, the appropriate compound can be administered depending on the period of pupil dilation time required.

Other aspects of this invention include practicing the method of this invention with a pharmaceutically acceptable ophthalmological carrier.

Hydrolysis of the diester produces the inactive adrenalone while a competing reduction - hydrolytic sequence resuls in adrenalin. While the inactive adrenalone is found in every compartment of the eye, the active epenephrine (adrenalin) is found only in the uveal (iris-ciliary body) tissues. Thus, topical adminstration of a compound of Formula I to the eye of an animal effectively induces pupil diameter enlargement and lowers intraocular pressure for a limited duration as a novel type of site-specific delivery system for epinephrine without the concomitant appearance of any significant undesirable side-effects associated with the prior art.

In accordance with the present invention, the compound of Formula I or an ophthalmologically acceptable acid addition salt thereof is applied topically to the eye in an effective ophthalmologically acceptable amount, thereby providing a useful diagnostic, surgical and/or therapeutic pupil diameter enlargement and intraocular pressure reduction.

It is to be understood that the term "effective ophthalmologically acceptable amount" as used herein generally refers to the quantity of the active ingredient necessary to effect a pupil diameter enlargement without causing any substantial concomitant side effects associated with the prior art as heretofore described. The administered dose, whether a single dose or a multiple dose, will, of course, vary with the compound administered and the individual treated, and is therefore not subject to definite bounds. However, upon reading the disclosure, those skilled in the art will be able to determine an effective amount, or the equivalent on a molar basis of the pharmacologically active form produced upon the metabolic release of the active drug to achieve its desired pharmacological and physiological effect, i.e., a short-term enlargement of pupil diameter and lowering of intraocular pressure. Normally, a dose from 50 to 100 microliters of a solution containing a concentration of active ingredient in an amount in the range of 0.01 to 2.0% in a single administration will suffice to effect a pupil diameter enlargement and a reduction in intraocular pressure. An active ingredient concentration in the range of 0.04 to 0.5% is preferred.

The term "ophthalmologically acceptable acid addition salts" as used herein in describing the salts of the compound of Formula I is intended to define those salts which are nontoxic and nonirritating on topical application to the eye, stable when stored, and otherwise generally acceptable for ophthalmic formulation. By way of example, there can be mentioned those salts derived from organic or inorganic acids which are nonirritating to the ophthalmic membrane such as hydrochloric, hydrobromic, sulfric, phosphoric, methanesulfonic, acetic, citric, malic, succinic, lactic, tartaric, benzoic and the like.

When the compound of Formula I is administered topically to the eye of an animal, it is preferred to maintain the same in a aqueous isotonic vehicle such as a 0.9% sodium chloride solution. Normally one to four drops of such solution is sufficient for inducing pupil diameter enlargement and reducing intraocular pressure. Naturally, other vehicles and additional active ingredients may be included, provided they do not hinder the activity of the main active drug, the compound encompassed by general Formula I, as a diagnostic, surgical and/or therapeutic agent.

In practicing the method of the present invention, ophthalmologically acceptable acid addition salts of the compound of Formula I which are exceptionally water soluble, such as the tartrate, bitartrate, sulfate or hydrochloride salts are preferred.

In practicing the present invention, the ophthalmologist involved should determine the particular compound to be used, its amount and concentration based on the amount of time he will require the pupil to remain dialated. If all factors are correctly considered, normal eyesight should be restored very shortly after the ophthalmologist has completed any task, such as an eye examination, that he wishes to carry out.

Without further elaboration, it is believed that one of ordinary skill in the art can, using the preceding description, utilize the present invention to its fullest extent. Consequently, the following specific embodiments are, therefore, to be construed as merely illustrative, and not limitative, of the remainder of the specification and claims in any way whatsoever.

EXAMPLE I

Mydriasis Evaluation Using 0,0-Di(Ethylsuccinyl) Adrenalone Hydroperchlorate

Preparation of 0,0-Di(Ethylsuccinyl) Adrenalone Hydroperchlorate

To a solution of 2.5 g of adrenalone hydrochloride (1) (0.01 mole) in 15 ml ethyl acetate, 15 ml ethyl succinyl chloride and 1.43 g 70% perchloric acid were added dropwise. The mixture was refluxed for 5 hours and covered with a continuous stream of nitrogen. After cooling to room temerature and removal of solvent, a yellow oil as obtained.

Purification of this compound was accomplished using CC-7 neutral silica and a chloroform/methanol (20 $CHCl_3$: 1 $CH_3OH$) mobile phase. A solid white compound was obtained, which was recrystalized from isopropyl alcohol; m.p. 95°-98° C.; $^1H$-NMR ($CDCl_3$) 1.22 (6H, t, J=8Hz, $2XOCH_2CH_3$); 2.50-3.0 (11H, M, 2X—$COCH_2CH_2CO$—); and —$NHCH_3$) 4.10 (4H, q, J=8Hz, 2X—$OCH_2CH_3$), 4.60 (2H, brs,—$COCH_2$—N—H—($CH_3$)), 7.2-7.8 (3H, M, aromatic proton). IR (KBr) 1750, 1715, 1680, 1400, 1355, 1310, 1250, 1100(br), 1005 and 800 $cm^{-1}$. Anal. calcd. for $C_{21}H_{27}NO_9HClO_4$ (mw=537.902): C,46.89; H, 5.25; N, 2.60; Cl, 6.59; Found: C,46.84; H, 5.23; M, 2.58; Cl,6.57.

Compounds 0,0-bis(N,N- diethylsuccinamyl) adrenalone hydrochloride and 0,0-dicinnamoyladrenalone hydrochloride were prepared accordingly to the methods described by Bodor and Visor, *Pharm. Res,* 4, 168-173 (1984), incorporated herein by reference.

Mydriatic Studies Methods and Material

Normal New Zealand male albino rabbits weighing from 2 to 3 kg. were used in the studies. The animals were placed in fiberglass restraining cages at least a half hour before the experiment and remained there throughout the test. The cages were located in a light and temperature controlled room. Pupil diameter was measured with a monostat vernier caliper held at a constant distance from observer and animal eyes. Drug solutions were formulated by dissolving the test agent in 0.9% saline solutions.

In the test procedure, a standard dose volume of 0.05 ml of the drug solution was applied to one eye and 0.9% saline was applied to the other eye of the same animal. The differences in the same animals between pupil diameter in millimeters of the eye with drug applied against the other eye with only saline instilled were recorded.

The pupillary dose response results are shown below in Table I.

TABLE I
THE EFFECT OF 0,0-DI(ETHYLSUCCINYL) ADRENALONE HYDROPERCHLORATE ON PUPIL DIAMETER IN NORMAL ALBINO RABBITS

| Concen- | Time (minutes) | | | | | |
|---|---|---|---|---|---|---|
| tration | 10 | 20 | 30 | 60 | 120 | 180 |
| | Pupil Diameter (X ± S.E.) | | | | | |
| $2.4 \times 10^{-3}$ M | 0.15 ± 0.06 | 0.18 ± 0.06 | 0.20 ± 0.12 | 0.30 ± 0.10 | 0.08 ± 0.02 | 0.11 ± 0.06 |
| $5.0 \times 10^{-3}$ M | 0.20 ± 0.06 | 0.56 ± 0.10 | 0.82 ± 0.22 | 0.78 ± 0.36 | 0.46 ± 0.27 | 0.58 ± 0.21 |
| $1.0 \times 10^{-2}$ M | 0.34 ± 0.14 | 0.43 ± 0.11 | 1.27 ± 0.53 | 1.42 ± 0.31 | 0.18 ± 0.09 | 0.37 ± 0.31 |
| $1.5 \times 10^{-2}$ M | 0.33 ± 0.08 | 0.80 ± 0.10 | 1.10 ± 0.04 | 2.13 ± 0.15 | 0.34 ± 0.12 | 0.16 ± 0.06 |
| $2.0 \times 10^{-2}$ M | 0.69 ± 0.11 | 1.12 ± 0.27 | 1.64 ± 0.21 | 3.11 ± 0.15 | 0.79 ± 0.30 | 0.31 ± 0.12 |
| $2.5 \times 10^{-2}$ M | 0.44 ± 0.16 | 1.99 ± 0.18 | 2.90 ± 0.16 | 3.29 ± 0.16 | 1.66 ± 0.11 | 0.22 ± 0.07 |

When the preceding example is repeated, but this time, employing any one of the remaining compounds encompassed within Formula I, substantially similar results will be observed.

In addition to providing the short-term pupil diameter enlargement in accordance with the present invention, these compounds of Formula I should be very active in reducing intraocular pressure due to the observed mydriatic response and relative sympathomimetic activities displayed by other adrenalone derivatives tested by Bodor, Kaminski, and Roller, *Int. J. Pharmaceutics*, 1, 189–196 (1978).

The hydrolytic behavior of the ethyl succinyl derivative in ocular tissues, human plasma, and isotonic saline buffer pH 7.4 at 37° C. was measured to determine enzymatic activity, and the results expressed at the t ½ life. The stability of the ethyl succinyl derivative in isotonic saline buffer was determined in order to contrast the rates of hydrolysis of a chemical system with those of the ocular enzymatic systems. Ocular tissues were obtained from New Zealand albino rabbits. Homogenates were prepared in isotonic saline with a potassium phosphate buffer pH 7.4. High pressure liquid chromatography systems with spectrophotometric (254 nm) and electrochemical detection were used for determination.

The results are listed in Table II shown below.

TABLE II
ENZYMATIC HYDROLYSIS OF 0,0-DI(ETHYLSUCCINYL) ADRENALONE HYDROPERCHLORATE IN VARIOUS MEDIA AT 37° C.

| Media | k (min$^{-1}$ × 10$^{-1}$) | r | t ½ (min) |
|---|---|---|---|
| Iris/ciliary body 10% homogenate | 7.91 | 0.9900 | 0.88 |
| Aqueous humor | 5.09 | 0.9995 | 1.36 |
| Corneal tissue 10% homogenate | 3.08 | 0.9929 | 2.25 |
| Human plasma | 6.68 | 0.9998 | 1.01 |
| Isotonic saline pH 7.4 | 0.04 | 0.9988 | 173 |

Pharmaceutical compositions comprising any of the compounds of Formula I in combination with a nontoxic pharmaceutically acceptable ophthalmological carrier is preferred for practicing the present invention. These include ophthalmic solutions, ointments or any other equivalent ophthalmic vehicles. Aqueous ophthalmic solutions formulated in accordance with good pharmaceutical practices as set forth in Chapter 83 of Remington's Pharmaceutical Sciences, Fourteenth Edition, Mac Publishing Company, are preferred although petrolatum based ointments may suffice. The ophthalmic solutions are naturally sterilized and preferably contain a bacterilogical preservative to maintain sterility during storage and use. The quaternary ammonium bacteriostats such as benzalkonium chloride are satisfactory. Antioxidants can also be employed if desirable, but in view of the fact that the compounds of Formula I are highly stable toward degradation, antioxidants will seldom be necessary. By way of example, suitable antioxidants include sodium bisulfite, N-acetylcystene salts, sodium ascorbate and other water soluble ophthalmologically acceptable antioxidants known in the pharmaceutical arts.

Ophthalmic solutions of any of the compounds of Formula I may be adjusted with inert ingredients such as sodium chloride or boric acid to provide a solution which is comfortable for application to the eye. That is, adding ingredients to the basic ophthalmological formulation for the purpose of achieving isotonicity with the eye are within the purview of the instant invention.

Ointments are prepared with conventional petrolatum vehicles employing liquid petrolatum and white petrolatum in such proportions as to afford an ointment of desirable fluidity.

From the foregoing description, one of ordinary skill in the art can easily ascertain the essential characteristics of this invention, and without departing from the spirit and scope thereof, can make various changes and/or modifications to the invention for adopting it to various usages and conditions. Accordingly, such changes and modifications are properly, equitably and intended to be, within the full range of equivalence of the claims.

What I claim is:

1. A method of inducing pupil diameter enlargement in a subject, comprising topically administering to the eye of the subject an amount effective for inducing pupil diameter enlargement of an adrenalone diester compound of the general formula:

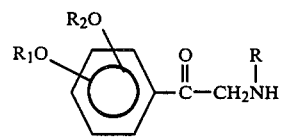

wherein R represents hydrogen or a straight chain alkyl of 1 to 3 carbon atoms, and $R_1$ and $R_2$ are the same or different and are selected from the group consisting of:

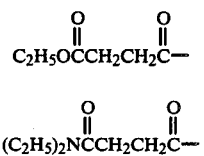

and

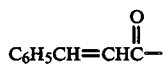

or an ophthalmologically acceptable acid addition salt thereof.

2. A method as claimed in claim 1, wherein said compound is:
0,0-di(ethylsuccinyl) adrenalone hydroperchlorate.

3. A method as claimed in claim 1, wherein said compound is:
0,0-bis(N,N-diethylsuccinamyl) adrenalone hydrochloride.

4. A method as claimed in claim 1, wherein said compound is:
0,0-dicinnamoyl-adrenalone hydrochloride.

5. A method as claimed in claim 1, wherein said compound is administered in combination with a non-toxic pharmaceutically acceptable ophthalmological carrier.

6. A method as claimed in claim 5, wherein said carrier is an isotonic aqueous sodium chloride solution.

7. A method as claimed in claim 5, wherein said compound is present in the carrier in a concentration of from 0.01 to 2.0%.

8. A method as claimed in claim 5, wherein said compound is present in the carrier in a concentration of from 0.04 to 0.5%.

9. A method as claimed in claim 6, wherein said compound is present in the carrier in a concentration of from 0.01 to 2.0%.

10. A method as claimed in claim 6, wherein said compound is present in the carrier in a concentration of from 0.04 to 0.5%.

11. A method as claimed in claim 1, wherein R is methyl.

12. A composition for inducing pupil diameter enlargement in a subject, comprising: an adrenalone diester compound of the general formula:

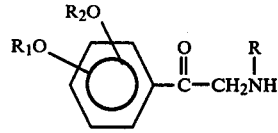

wherein R represents a member selected from the group consisting of hydrogen or a straight chain alkyl of 1 to 3 carbon atoms, and $R_1$ and $R_2$ are the same or different and are selected from the group consisting of:

and

or an ophthalmologically acceptable acid addition salt thereof, in a concentration effective to induce pupil diameter enlargement thereof; and
a pharmaceutically acceptable ophthalmological carrier.

13. A composition as claimed in claim 12, wherein said compound is present in the carrier in a concentration of from 0.01 to 2.0%.

14. A composition as claimed in claim 13, wherein said compound is present in the carrier in a concentration of from 0.04 to 0.5%.

* * * * *